(12) United States Patent
Wu et al.

(10) Patent No.: US 11,735,315 B2
(45) Date of Patent: Aug. 22, 2023

(54) METHOD, APPARATUS, AND DEVICE FOR FUSING FEATURES APPLIED TO SMALL TARGET DETECTION, AND STORAGE MEDIUM

(71) Applicant: BEIJING BAIDU NETCOM SCIENCE AND TECHNOLOGY CO., LTD., Beijing (CN)

(72) Inventors: Binghong Wu, Beijing (CN); Yehui Yang, Beijing (CN); Yanwu Xu, Beijing (CN); Lei Wang, Beijing (CN)

(73) Assignee: Beijing Baidu Netcom Science and Technology Co., Ltd., Beijing (CN)

( * ) Notice: Subject to any disclaimer, the term of this patent is extended or adjusted under 35 U.S.C. 154(b) by 313 days.

(21) Appl. No.: 17/213,896

(22) Filed: Mar. 26, 2021

(65) Prior Publication Data
US 2021/0224581 A1 Jul. 22, 2021

(30) Foreign Application Priority Data
Sep. 25, 2020 (CN) .......................... 202011021013.9

(51) Int. Cl.
*G16H 30/40* (2018.01)
*G06F 18/25* (2023.01)
(Continued)

(52) U.S. Cl.
CPC ........... *G16H 30/40* (2018.01); *G06F 18/251* (2023.01); *G06F 18/253* (2023.01); *G06N 3/045* (2023.01);
(Continued)

(58) Field of Classification Search
CPC ...... G16H 30/40; G16H 50/20; G06F 18/251; G06F 18/253; G06N 3/045; G06N 3/08;
(Continued)

(56) References Cited

U.S. PATENT DOCUMENTS

2020/0334819 A1* 10/2020 Chen .................... G06V 10/454
2021/0365717 A1* 11/2021 Cao ........................... G06N 3/08
(Continued)

OTHER PUBLICATIONS

Z. Xue, W. Chen and J. Li, "Enhancement and Fusion of Multi-Scale Feature Maps for Small Object Detection," 2020 39th Chinese Control Conference (CCC), Shenyang, China, 2020, pp. 7212-7217, doi: 10.23919/CCC50068.2020.9189352. (Year: 2020).*

*Primary Examiner* — Fayyaz Alam
(74) *Attorney, Agent, or Firm* — Kilpatrick Townsend & Stockton LLP (57) ABSTRACT

Embodiments of the present disclosure disclose a method, apparatus, and device for fusing features applied to small target detection, and a storage medium, relate to the field of computer vision technology. A particular embodiment of the method for fusing features applied to small target detection comprises: acquiring feature maps output by convolutional layers in a Backbone network; performing convolution on the feature maps to obtain input feature maps of feature layers, the feature layers representing resolutions of the input feature maps; and fusing, based on densely connection feature pyramid network features, the input feature maps of each feature layer to obtain output feature maps of the feature layer. Since no additional convolutional layer is introduced for feature fusion, the detection performance for small targets may be enhanced without additional parameters, and the detection ability for small targets may be improved with computing resource constraints.

15 Claims, 5 Drawing Sheets (51) Int. Cl.
  *G06N 3/045* (2023.01)
  *G06V 10/764* (2022.01)
  *G06V 10/80* (2022.01)
  *G06V 10/82* (2022.01)
  *G16H 50/20* (2018.01)
(52) U.S. Cl.
  CPC .......... *G06V 10/764* (2022.01); *G06V 10/806* (2022.01); *G06V 10/82* (2022.01); *G16H 50/20* (2018.01)
(58) Field of Classification Search
  CPC .... G06V 10/764; G06V 10/806; G06V 10/82; G06V 2201/07
  See application file for complete search history.

(56) References Cited

U.S. PATENT DOCUMENTS

| | | | |
|---|---|---|---|
| 2021/0398252 A1* | 12/2021 | Song | G06T 5/50 |
| 2022/0051405 A1* | 2/2022 | Luo | G06N 3/04 |

* cited by examiner

METHOD, APPARATUS, AND DEVICE FOR FUSING FEATURES APPLIED TO SMALL TARGET DETECTION, AND STORAGE MEDIUM

CROSS-REFERENCE TO RELATED APPLICATIONS

This application claims priority to Chinese Patent Application No. 202011021013.9, filed with the China National Intellectual Property Administration (CNIPA) on Sep. 25, 2020, the contents of which are incorporated herein by reference in their entirety.

TECHNICAL FIELD

The present disclosure relates to the field of computer technology, particularly to the field of computer vision technology, applicable to medical image analysis, and more particularly to a method, apparatus, and device for fusing features applied to small target detection, and relates to a storage medium.

BACKGROUND

Intelligent fundus screening system refers to an intelligent diagnosis system that autonomously makes a result that meets a doctor's diagnosis based on fundus photo information of a subject and with auxiliary reference to the subject's related physical conditions (such as blood pressure, blood glucose), without professional ophthalmologist's experience instructions or guidance.

The intelligent fundus screening system may use an autonomous decision-making method on a local terminal, that is, a to-be-screened picture is directly used on a local intelligent terminal for diagnosis and decision-making. This diagnosis method does not depend on the network environment and may directly feed back diagnosis results, but may have a huge test on the complexity of the intelligent diagnosis system and the real-time performance with limited computing power. The conventional screening of fundus diseases (such as diabetic retinopathy grade 1) often relies on the detection for small targets (microangiomas, bleeding spots), so it is very important to improve the detection accuracy for small targets as much as possible with limited resources.

SUMMARY

Embodiments of the present disclosure provide a method, apparatus, and device for fusing features applied to small target detection, and a storage medium.

In a first aspect, embodiments of the present disclosure provide a method for fusing features applied to small target detection, comprising: acquiring feature maps output by convolutional layers in a Backbone network; performing convolution on the feature maps to obtain input feature maps of feature layers, the feature layers representing resolutions of the input feature maps; and fusing, based on densely connection feature pyramid network features, the input feature maps of each feature layer to obtain output feature maps of the feature layer, comprising: sampling an input feature map of an $i^{th}$ feature layer and input feature maps of other feature layers having resolutions lower than a resolution corresponding to the $i^{th}$ feature layer, i being a positive integer; scaling, after the sampling, the input feature maps of the other feature layers to a same size as the input feature map of the $i^{th}$ feature layer; and superimposing the input feature maps of the other feature layers after scaling and the input feature map of the $i^{th}$ feature layer one by one, and using a superimposed final result as an output feature map of the $i^{th}$ feature layer.

In a second aspect, embodiments of the present disclosure provide an apparatus for fusing features applied to small target detection, comprising: an acquisition module, configured to acquire feature maps output by convolutional layers in a Backbone network; a dimension compression module, configured to perform convolution on the feature maps to obtain input feature maps of feature layers, the feature layers representing resolutions of the input feature maps; and a densely connection feature pyramid network feature fusion module, configured to fuse, based on densely connection feature pyramid network features, the input feature maps of each feature layer to obtain output feature maps of the feature layer, comprises: sampling an input feature map of an $i^{th}$ feature layer and input feature maps of other feature layers having resolutions lower than a resolution corresponding to the $i^{th}$ feature layer, i being a positive integer; scaling, after the sampling, the input feature maps of the other feature layers to a same size as the input feature map of the $i^{th}$ feature layer; and superimposing the input feature maps of the other feature layers after scaling and the input feature map of the $i^{th}$ feature layer one by one, and using a superimposed final result as an output feature map of the $i^{th}$ feature layer.

In a third aspect, embodiments of the present disclosure provide an electronic device, comprising: one or more processors; and a memory, storing one or more programs, wherein the one or more programs, when executed by the one or more processors, cause the one or more processors to implement the method for fusing features applied to small target detection provided by the first aspect.

In a forth aspect, embodiments of the present disclosure provide a computer-readable medium, storing a computer program thereon, wherein the program, when executed by a processor, causes the processor to implement the method for fusing features applied to small target detection provided by the first aspect.

The method, apparatus, and device for fusing features applied to small target detection, and a storage medium provided by the embodiments of the present disclosure, first acquiring feature maps output by convolutional layers in a Backbone network; then performing convolution on the feature maps to obtain input feature maps of feature layers, the feature layers representing resolutions of the input feature maps; and finally fuse, based on densely connection feature pyramid network features, the input feature maps of each feature layer to obtain output feature maps of the feature layer. Since no additional convolutional layer is introduced for feature fusion, the detection performance for small targets may be enhanced without additional parameters, and the detection ability for small targets may be improved with computing resource constraints.

It should be understood that the content described in this section is not intended to identify key or important features of the embodiments of the present disclosure, nor is it intended to limit the scope of the present disclosure. Other features of the present disclosure will be easily understood by the following description.

BRIEF DESCRIPTION OF THE DRAWINGS

After reading detailed descriptions of non-limiting embodiments with reference to the following accompanying drawings, other features, objectives and advantages of the present disclosure will become more apparent. The accompanying drawings are used to better understand the present solution and do not constitute a limitation to the present disclosure, in which.

DETAILED DESCRIPTION OF EMBODIMENTS

The present disclosure will be further described in detail below with reference to the accompanying drawings and embodiments. It may be understood that the particular embodiments described herein are only used to explain the related disclosure, but not to limit the disclosure. In addition, it should also be noted that, for ease of description, only parts related to the relevant disclosure are shown in the accompanying drawings.

It should be noted that the embodiments in the present disclosure and the features in the embodiments may be combined with each other on a non-conflict basis. The present disclosure will be described below in detail with reference to the accompanying drawings and in combination with the embodiments.

Figure 1:
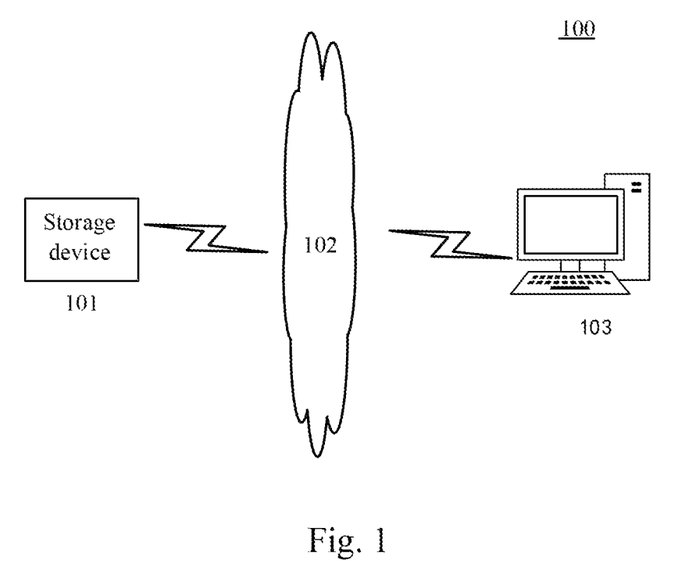
FIG. 1 is a diagram of an exemplary system architecture in which the present disclosure may be implemented.

FIG. 1 illustrates an exemplary system architecture 100 of an embodiment of a method for fusing features applied to small target detection or an apparatus for fusing features applied to small target detection in which the present disclosure may be implemented.

As shown in FIG. 1, the exemplary system architecture 100 may comprise a storage device 101, a network 102, and a computer 103. The network 102 is used to provide a communication link medium between the storage device 101 and the computer 103. The network 102 may comprise various types of connections, such as wired, wireless communication links, or optic fibers.

The storage device 101 may interact with the computer 103 through the network 102. Fundus pictures may be provided in the storage device 101, comprising but not limited to databases, user terminals, and so on.

The storage device 101 may also interact with the computer 103 in an offline status (for example, disconnected from the network 102). For example, data in the storage device 101 are transferred to the computer 103. Exemplarily, the storage device 101 may be a mobile hard disk, a mobile magnetic disk, a U disk, or the like.

The computer 103 may provide various services. For example, the computer 103 may perform small target detection on a fundus picture acquired from the storage device 101, and generate a processing result (for example, fusing, based on densely connection feature pyramid network features, the input feature maps of each feature layer in the fundus picture).

It should be noted that the method for fusing features applied to small target detection provided by the embodiments of the present disclosure is generally performed by the computer 103. Accordingly, the apparatus for fusing features applied to small target detection is generally provided in the computer 103.

It should be understood that the number of storage devices, networks and computers in FIG. 1 is merely illustrative. Depending on the implementation needs, there may be any number of storage devices, networks and computers.

Figure 2:
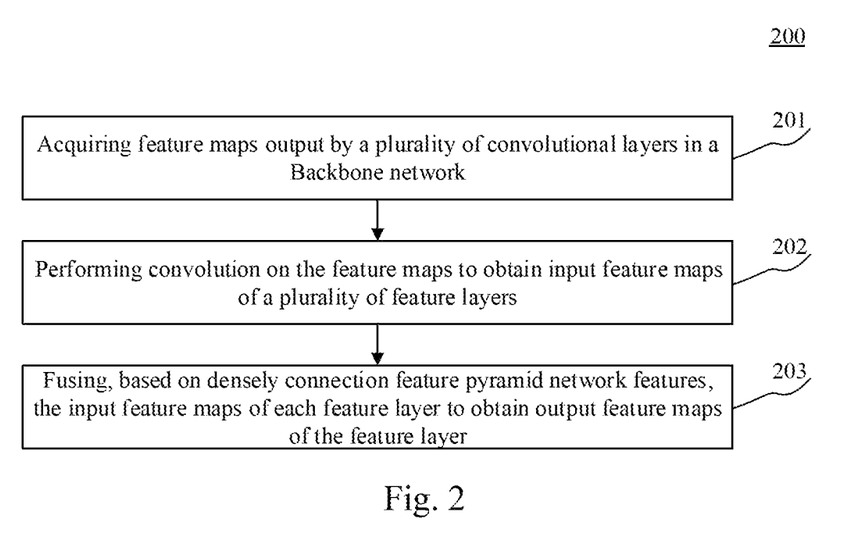
FIG. 2 is a schematic flowchart of an embodiment of a method for fusing features applied to small target detection according to the present disclosure.

With further reference to FIG. 2, a flow 200 of an embodiment of a method for fusing features applied to small target detection according to the present disclosure is illustrated. The method for fusing features applied to small target detection comprises the following steps:

Step 201, acquiring feature maps output by a plurality of convolutional layers in a Backbone network.

In the present embodiment, an executing body of the method for fusing features applied to small target detection (for example, the computer 103 shown in FIG. 1) may acquire the feature maps output by the plurality of convolutional layers in the Backbone network. In the field of computer vision technology, Backbone network refers to a basic network structure in deep learning, comprising but not limited to AlexNet, ResNet, DenseNet, EfficientNet, etc. After entering a neural network model, an image first enters the Backbone network for feature extraction to obtain a feature map (Featuremap) of the image.

In some alternative implementations of the present embodiment, extracting feature maps of last N convolutional layers from the Backbone network and using the extracted feature maps as feature maps output by the convolutional layers, where N is a positive integer. For example, feature maps of the last 3 convolutional layers $C_3$, $C_4$, and $C_5$ may be extracted from the Resnet network as the feature maps output by the convolutional layers. The last N convolutional layers in the Backbone network comprise more subtle feature information of image. Using the information as output features of the convolutional layers helps to improve the detection ability for small targets in the image.

Step 202, performing convolution on the feature maps to obtain input feature maps of a plurality of feature layers.

In the present embodiment, the executing body may obtain the input feature maps of the plurality of feature layers based on the feature maps using convolution. The plurality of feature layers represent a plurality of resolutions of the input feature maps. By performing convolution calculation on the feature maps output by the convolutional layers, the number of channels of the feature maps may be changed, and the dimension of the feature maps may then be compressed. Exemplarily, the feature maps output by the third convolutional layer $C_3$, the fourth convolutional layer $C_4$, and the fifth convolutional layer $C_5$ in the ResNet network are used as input, and the input feature maps $P_{3\_in}$, $P_{4\_in}$, and $P_{5\_in}$ of three feature layers are output through 1×1 convolution. The number of channels of the feature maps of the convolutional layers in the ResNet network may be unified from 512, 1024, and 2048 to 255 through the 1×1 convolution.

In the present embodiment, the above plurality of feature layers may be a plurality of feature layers in a feature pyramid networks (FPN) or a bi-directional feature pyramid networks (BiFPN) from high level feature layer to low level feature layer. Here, high level feature maps and low level feature maps reflect different levels of information of image. High level feature maps are feature maps having lower resolutions, and low level feature maps are feature maps having higher resolutions. Particularly, a plurality of feature maps from the high level feature maps to the low level feature maps may be used as the input feature maps of the above plurality of feature layers.

In some alternative implementations of the present embodiment, in order to obtain features of a larger receptive field, convolution calculation may be continuously performed on the high level feature maps that have been obtained, comprising the following steps: performing convolution calculation on the feature maps output by the convolutional layers to obtain input feature maps of N feature layers corresponding to the convolutional layers; performing convolution calculation on an input feature map of a feature layer representing the lowest resolution to obtain an input feature map of the $N+1^{th}$ feature layer; and performing convolution calculation on the input feature map of the $N+1^{th}$ feature layer to obtain an input feature map of the $N+2^{th}$ feature layer.

Exemplarily, the feature maps output by the third convolutional layer $C_3$, the fourth convolutional layer $C_4$, and the fifth convolutional layer $C_5$ in the ResNet network are used as input, and the input feature maps $P_{3\_in}$, $P_{4\_in}$, $P_{5\_in}$ of the three feature layers are output through 1×1 convolution, then convolution is continuously performed on the smallest feature map $P_{5\_in}$ (the feature map having the lowest resolution) to obtain the input feature map $P_{6\_in}$ of the fourth feature layer, and then convolution is continuously performed on the input feature map $P_{6\_in}$ to obtain the input feature map $P_{7\_in}$ of the fifth feature layer.

Step 203, fusing, based on densely connection feature pyramid network features, the input feature maps of each feature layer to obtain output feature maps of the feature layer.

In the present embodiment, the executing body may fuse, based on densely connection feature pyramid network features, the input feature maps of each feature layer to obtain output feature maps of the feature layer. Feature fusion is an important method to implement feature reuse. In the structural design of a target detection model, how to integrate multi-scale information is the key to improving detection performance. FPN uses a top-down connection, and implements feature fusion by up-sampling low-resolution features and adding them to high-resolution feature maps. However, using the FPN fusion method, features of the fusion layer are only connected to an adjacent layer. Therefore, there is a problem that the lowest-level features may not directly acquire top-level features, which affects detection accuracy. PANet is further deepened on the basis of FPN, by adding an additional convolutional layer, high-resolution fused features are fused to low resolution again. BiFPN implements feature fusion by cascading a plurality of FPNs and adding a layer jump connection in a plurality of cascading modules. Both PANet and BiFPN perform multi-scale feature fusion by adding additional convolutional layer, so the number of parameters has a significant increase compared with FPN, which may cause a great burden on local smart devices without relying on the network environment.

The embodiments of the present disclosure propose a novel feature fusion method—densely connection feature pyramid network (DCFPN). The particular integration method is as follows: sampling an input feature map of the $i^{th}$ feature layer and input feature maps of other feature layers having resolutions lower than a resolution corresponding to the $i^{th}$ feature layer, i being a positive integer; scaling, after the sampling, the input feature maps of the other feature layers to the same size as the input feature map of the $i^{th}$ feature layer; and superimposing the input feature maps of the other feature layers after scaling and the input feature map of the $i^{th}$ feature layer one by one, and using a superimposed final result as an output feature map of the $i^{th}$ feature layer.

Figure 3:
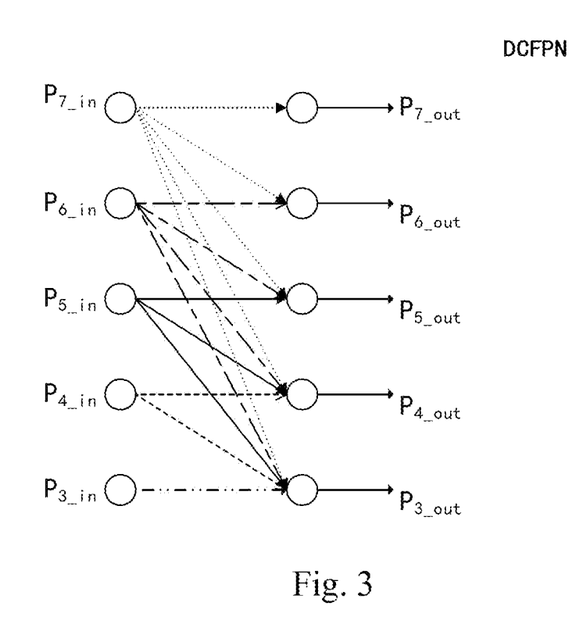
FIG. 3 is an application embodiment of a densely connection feature pyramid network according to an embodiment of the present disclosure.

In order to facilitate understanding of the DCFPN feature fusion method, FIG. 3 shows an application embodiment of DCFPN according to an embodiment of the present disclosure.

As shown in FIG. 3, for example, there are 5 feature layers in total, in the order from low level feature layer to high level feature layer, they are the third feature layer, the fourth feature layer, the fifth feature layer, the sixth feature layer, and the seventh feature layer in sequence. The input feature map $P_{3\_in}$ of the third feature layer has the highest resolution, and the input feature map $P_{7\_in}$ of the seventh feature layer has the lowest resolution. For the third feature layer, the output feature map $P_{3\_out}$ is obtained as follows:

sampling the input feature map $P_{3\_in}$ of the third feature layer and the input feature maps $P_{7\_in}$, $P_{6\_in}$, $P_{5\_in}$, and $P_{4\_in}$ of the seventh feature layer, the sixth feature layer, the fifth feature layer, and the fourth feature layer; scaling the sampled input feature maps $P_{7\_in}$, $P_{6\_in}$, $P_{5\_in}$, and $P_{4\_in}$ to the same size as the input feature map $P_{3\_in}$ of the third feature layer; and superimposing the scaled input feature maps $P_{7\_in}$, $P_{6\_in}$, $P_{5\_in}$, and $P_{4\_in}$ on the input feature map $P_{3\_in}$ one by one, as the final output feature map $P_{3\_out}$ of the third feature layer.

Compared with the prior art, the embodiments of the present disclosure enhance the detection performance for small targets without additional parameters, and improve the detection rate of detection model for small targets with computing resource constraints, thereby improving the success rate of early screening of a fundus intelligent diagnosis system.

Figure 4:
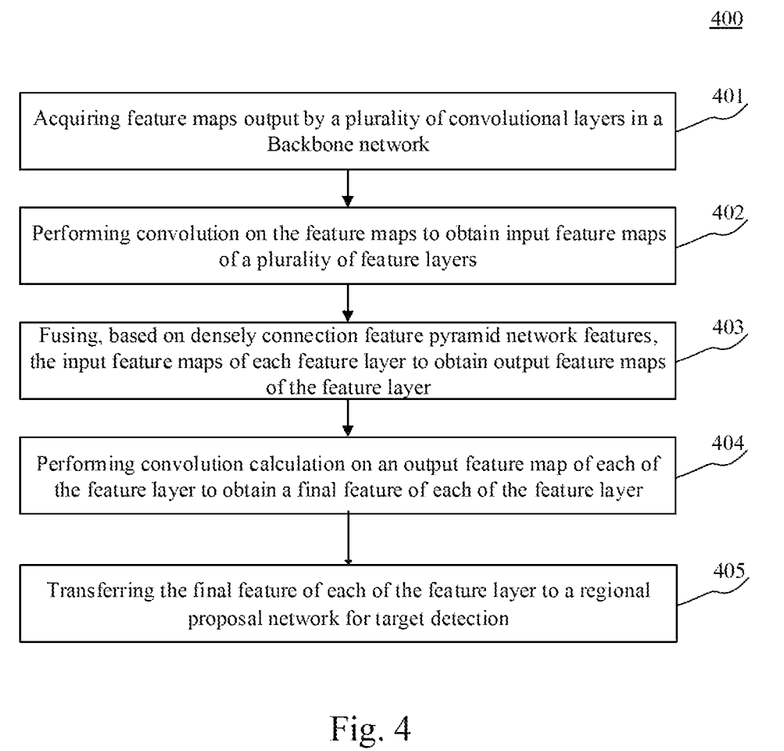
FIG. 4 is a flowchart of another embodiment of the method for fusing features applied to small target detection according to the present disclosure.

With further reference to FIG. 4, a flow 400 of another embodiment of the method for fusing features applied to small target detection according to the present disclosure is illustrated.

As shown in FIG. 4, steps 401, 402, and 403 in the method are the same in particular processing and technical effects of steps 201-203 in FIG. 2, and detailed description thereof will be omitted.

As shown in FIG. 4, the method further comprises:

Step 404, performing convolution calculation on an output feature map of each of the feature layer to obtain a final feature of each of the feature layer.

In the present embodiment, the executing body may perform convolution calculation on the output feature map of each of the feature layer to obtain the final feature of each of the feature layer. Exemplarily, the output feature map of each of the feature layer may be input to a "3×3 convolution" module in FPN or BiFPN, and then 3×3 convolution may be performed on the output feature map of each feature layer, and a result after the 3×3 convolution may be used as the final feature of each feature layer.

Step 405, transferring the final feature of each of the feature layer to a regional proposal network for target detection.

In the present embodiment, the executing body may transfer the final feature of each of the feature layer to the regional proposal network for target detection. The regional proposal network (RPN) is an anchor detector with a fixed window size, configured to generate proposals. Particularly, the RPN part in Faster R-CNN may be used.

In order to verify the effectiveness of the embodiments of the present disclosure, the following is a comparison of the effects of FPN and DCFPN based on a universal detection data set COCO. Here, AP (Average Precision, detection frame-level average accuracy) indicators are as follows:

| | neck | AP | $AP_{50}$ | $AP_{75}$ | $AP_S$ | $AP_M$ | $AP_L$ |
|---|---|---|---|---|---|---|---|
| RetinaNet-r50 | FPN | 0.363 | 0.553 | 0.386 | 0.193 | 0.400 | 0.488 |
| RetinaNet-r50 | DCFPN | 0.370 | 0.556 | 0.386 | 0.200 | 0.402 | 0.478 |

This experiment uses RetinaNet (Backbone: ResNet 50) as the baseline, and compares RetinaNet using FPN and RetinaNet using DCFPN for training, and performs performance verification on the COCO verification set. By comprehensive analysis of the table data, using a feature reuse mechanism, the DCFPN proposed in the present disclosure may improve the performance of the detector without introducing additional parameters. In addition, according to the three indicators of $AP_S$, $AP_M$ and $AP_L$, since the $AP_S$ and $AP_M$ of DCFPN are better than FPN, the corresponding indicators represent corresponding indicators of the detector in the case of small target and medium target subsets. Therefore, the gain of the overall improvement of model performance is mainly derived from the improvement of small target indicators.

Figure 5:
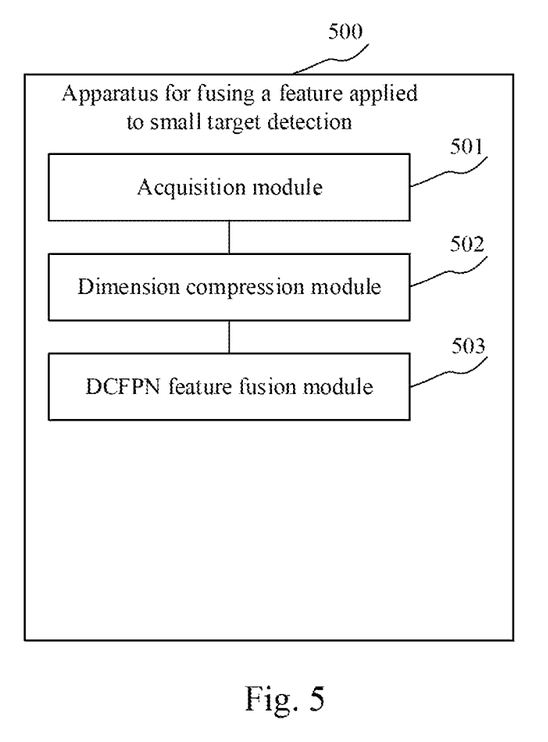
FIG. 5 is a schematic structural diagram of an embodiment of an apparatus for fusing features applied to small target detection of the present disclosure.

With further reference to FIG. 5, as an implementation of the method shown in the above figures, the present disclosure provides an embodiment of an apparatus for fusing features applied to small target detection, and the apparatus embodiment corresponds to the method embodiment as shown in FIG. 2. The apparatus may be particularly applied to various electronic devices.

As shown in FIG. 5, an apparatus 500 for fusing features applied to small target detection of the present embodiment may comprise: an acquisition module 501, a dimension compression module 502, and a densely connection feature pyramid network feature fusion module 503. The acquisition module 501 is configured to acquire feature maps output by a plurality of convolutional layers in a Backbone network. The dimension compression module 502 is configured to perform convolution on the feature maps to obtain input feature maps of a plurality of feature layers, the plurality of feature layers representing a plurality of resolutions of the input feature maps. The densely connection feature pyramid network feature fusion module 503 is configured to fuse, based on densely connection feature pyramid network features, the input feature maps of each feature layer to obtain output feature maps of the feature layer, comprises: sampling an input feature map of the $i^{th}$ feature layer and input feature maps of other feature layers having resolutions lower than a resolution corresponding to the $i^{th}$ feature layer, i being a positive integer; scaling, after the sampling, the input feature maps of the other feature layers to the same size as the input feature map of the $i^{th}$ feature layer; and superimposing the input feature maps of the other feature layers after scaling and the input feature map of the $i^{th}$ feature layer one by one, and using a superimposed final result as an output feature map of the $i^{th}$ feature layer.

In the present embodiment, in the apparatus 500 for fusing features applied to small target detection: the particular processing and technical effects thereof brought by the acquisition module 501, the dimension compression module 502, and the densely connection feature pyramid network feature fusion module 503 may be referred to the relevant descriptions of steps 201-203 in the embodiment corresponding to FIG. 2 respectively, and detailed description thereof will be omitted.

In some alternative implementations of the present embodiment, the acquisition module is further configured to: extract feature maps of last N convolutional layers from the Backbone network and use the extracted feature maps as feature maps output by the convolutional layers, where, N is a positive integer.

In some alternative implementations of the present embodiment, the dimension compression module is further configured to: perform convolution calculation on the feature maps output by the convolutional layers to obtain input feature maps of N feature layers corresponding to the convolutional layers; perform convolution calculation on an input feature map of a feature layer representing the lowest resolution to obtain an input feature map of the $N+1^{th}$ feature layer; and perform convolution calculation on the input feature map of the $N+1^{th}$ feature layer to obtain an input feature map of the $N+2^{th}$ feature layer.

In some alternative implementations of the present embodiment, the apparatus further comprises: a convolution module, configured to perform convolution calculation on an output feature map of each of the feature layer to obtain a final feature of each of the feature layer; and a target detection module, configured to transfer the final feature of the each feature layer to a regional proposal network for target detection.

Figure 6:
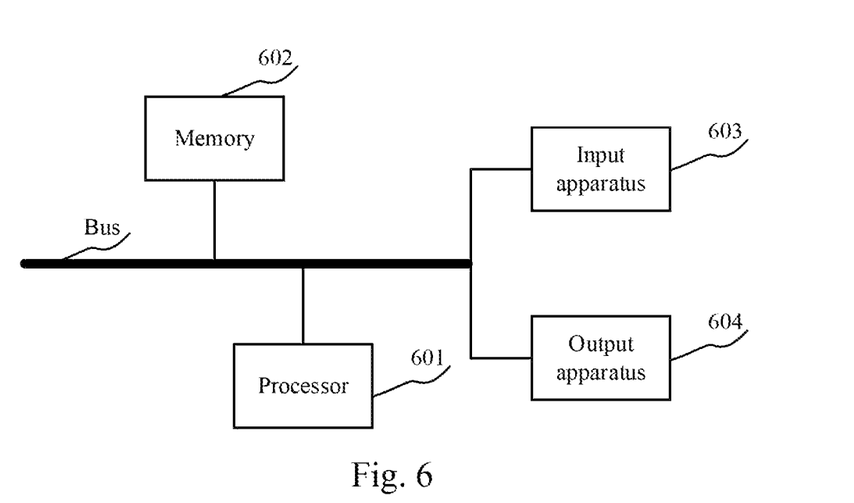
FIG. 6 is a block diagram of an electronic device used to implement the method for fusing features applied to small target detection according to an embodiment of the present disclosure.

As shown in FIG. 6, which is a block diagram of an electronic device of a method for fusing features applied to small target detection according to an embodiment of the present disclosure. The electronic device is intended to represent various forms of digital computers, such as laptop computers, desktop computers, workbenches, personal digital assistants, servers, blade servers, mainframe computers, and other suitable computers. The electronic device may also represent various forms of mobile apparatuses, such as personal digital processing, cellular phones, smart phones, wearable devices, and other similar computing apparatuses. The components shown herein, their connections and relationships, and their functions are merely examples, and are not intended to limit the implementation of the present disclosure described and/or claimed herein.

As shown in FIG. 6, the electronic device comprises: one or more processors 601, a memory 602, and interfaces for connecting various components, comprising high-speed interfaces and low-speed interfaces. The various components are connected to each other using different buses, and may be installed on a common motherboard or in other methods as needed. The processor may process instructions executed within the electronic device, comprising instructions stored in or on the memory to display graphic information of GUI on an external input/output apparatus (such as a display device coupled to the interface). In other embodiments, a plurality of processors and/or a plurality of buses may be used together with a plurality of memories if desired. Similarly, a plurality of electronic devices may be connected, and the devices provide some necessary operations (for example, as a server array, a set of blade servers, or a multi-processor system). In FIG. 6, one processor 601 is used as an example.

The memory 602 is a non-transitory computer readable storage medium provided by the present disclosure. The memory stores instructions executable by at least one processor, so that the at least one processor performs the method for fusing features applied to small target detection provided by the present disclosure. The non-transitory computer readable storage medium of the present disclosure stores computer instructions for causing a computer to perform the method for fusing features applied to small target detection provided by the present disclosure.

The memory 602, as a non-transitory computer readable storage medium, may be used to store non-transitory software programs, non-transitory computer executable programs and modules, such as program instructions/modules corresponding to the method for fusing features applied to small target detection in the embodiments of the present disclosure (for example, the acquisition module 501, the dimension compression module 502, and the densely connection feature pyramid network feature fusion module 503 shown in FIG. 5). The processor 601 executes the non-transitory software programs, instructions, and modules stored in the memory 602 to execute various functional applications and data processing of the server, that is, to implement the method for fusing features applied to small target detection in the foregoing method embodiment.

The memory 602 may comprise a storage program area and a storage data area, where the storage program area may store an operating system and at least one function required application program; and the storage data area may store data created by the use of the electronic device according to the method for fusing features applied to small target detection, etc. In addition, the memory 602 may comprise a high-speed random access memory, and may also comprise a non-transitory memory, such as at least one magnetic disk storage device, a flash memory device, or other non-transitory solid-state storage devices. In some embodiments, the memory 602 may optionally comprise memories remotely provided with respect to the processor 601, and these remote memories may be connected to the electronic device of the method for fusing features applied to small target detection through a network. Examples of the above network comprise but are not limited to the Internet, intranet, local area network, mobile communication network, and combinations thereof.

The electronic device of the method for fusing features applied to small target detection may further comprise: an input apparatus 603 and an output apparatus 604. The processor 601, the memory 602, the input apparatus 603, and the output apparatus 604 may be connected through a bus or in other methods. In FIG. 6, connection through a bus is used as an example.

The input apparatus 603 may receive input digital or character information, and generate key signal inputs related to user settings and function control of the electronic device of the method for fusing features applied to small target detection, such as touch screen, keypad, mouse, trackpad, touchpad, pointing stick, one or more mouse buttons, trackball, joystick and other input apparatuses. The output apparatus 604 may comprise a display device, an auxiliary lighting apparatus (for example, LED), a tactile feedback apparatus (for example, a vibration motor), and the like. The display device may comprise, but is not limited to, a liquid crystal display (LCD), a light emitting diode (LED) display, and a plasma display. In some embodiments, the display device may be a touch screen.

Various embodiments of the systems and technologies described herein may be implemented in digital electronic circuit systems, integrated circuit systems, dedicated ASICs (application specific integrated circuits), computer hardware, firmware, software, and/or combinations thereof. These various embodiments may comprise: being implemented in one or more computer programs that may be executed and/or interpreted on a programmable system that comprises at least one programmable processor. The programmable processor may be a dedicated or general-purpose programmable processor, and may receive data and instructions from a storage system, at least one input apparatus, and at least one output apparatus, and transmit the data and instructions to the storage system, the at least one input apparatus, and the at least one output apparatus.

These computing programs (also referred to as programs, software, software applications, or codes) comprise machine instructions of the programmable processor and may use high-level processes and/or object-oriented programming languages, and/or assembly/machine languages to implement these computing programs. As used herein, the terms "machine readable medium" and "computer readable medium" refer to any computer program product, device, and/or apparatus (for example, magnetic disk, optical disk, memory, programmable logic apparatus (PLD)) used to provide machine instructions and/or data to the programmable processor, comprising machine readable medium that receives machine instructions as machine readable signals. The term "machine readable signal" refers to any signal used to provide machine instructions and/or data to the programmable processor.

In order to provide interaction with a user, the systems and technologies described herein may be implemented on a computer, the computer has: a display apparatus for displaying information to the user (for example, CRT (cathode ray tube) or LCD (liquid crystal display) monitor); and a keyboard and a pointing apparatus (for example, mouse or trackball), and the user may use the keyboard and the pointing apparatus to provide input to the computer. Other types of apparatuses may also be used to provide interaction with the user; for example, feedback provided to the user may be any form of sensory feedback (for example, visual feedback, auditory feedback, or tactile feedback); and any form (comprising acoustic input, voice input, or tactile input) may be used to receive input from the user.

The systems and technologies described herein may be implemented in a computing system that comprises backend components (e.g., as a data server), or a computing system that comprises middleware components (e.g., application server), or a computing system that comprises frontend components (for example, a user computer having a graphical user interface or a web browser, through which the user may interact with the implementations of the systems and the technologies described herein), or a computing system that comprises any combination of such backend components, middleware components, or frontend components. The components of the system may be interconnected by any form or medium of digital data communication (e.g., communication network). Examples of the communication network comprise: local area networks (LAN), wide area networks (WAN), and the Internet.

The computer system may comprise a client and a server. The client and the server are generally far from each other and usually interact through the communication network. The relationship between the client and the server is generated by computer programs that run on the corresponding computer and have a client-server relationship with each other.

According to the technology of the present disclosure, first acquiring feature maps output by a plurality of convolutional layers in a Backbone network; then performing convolution on the feature maps to obtain input feature maps of a plurality of feature layers, the plurality of feature layers representing a plurality of resolutions of the input feature maps; and finally fusing, based on densely connection feature pyramid network features, the input feature maps of each feature layer to obtain output feature maps of the feature layer. Since no additional convolutional layer is introduced for feature fusion, the detection performance for small targets may be enhanced without additional parameters, and the detection ability for small targets may be improved with computing resource constraints.

It should be understood that the various forms of processes shown above may be used to reorder, add, or delete steps. For example, the steps described in the present disclosure may be performed in parallel, sequentially, or in different orders. As long as the desired results of the technical solution disclosed in the present disclosure may be achieved, no limitation is made herein.

The above particular embodiments do not constitute limitation on the protection scope of the present disclosure. Those skilled in the art should understand that various modifications, combinations, sub-combinations and substitutions may be made according to design requirements and other factors. Any modification, equivalent replacement and improvement made within the spirit and principle of the present disclosure shall be comprised in the protection scope of the present disclosure.

What is claimed is:

1. A method for fusing features applied to small target detection, the method comprising:
    acquiring feature maps output by convolutional layers in a Backbone network;
    performing a convolution on the feature maps to obtain input feature maps of feature layers, the feature layers representing resolutions of the input feature maps; and
    fusing, based on densely connection feature pyramid network features, the input feature maps of each feature layer to obtain output feature maps of the feature layers, the fusing comprising:
        sampling an input feature map of an $i^{th}$ feature layer and input feature maps of other feature layers having resolutions lower than a resolution corresponding to the $i^{th}$ feature layer, i being a positive integer;
        scaling, after the sampling, the input feature maps of the other feature layers to a same size as the input feature map of the $i^{th}$ feature layer; and
        superimposing the input feature maps of the other feature layers after scaling and the input feature map of the $i^{th}$ feature layer one by one, and using a superimposed final result as an output feature map of the $i^{th}$ feature layer.

2. The method according to claim 1, wherein, the acquiring comprises:
    extracting feature maps of last N convolutional layers from the Backbone network and using the extracted feature maps as feature maps output by the convolutional layers, wherein, N is a positive integer.

3. The method according to claim 2, wherein performing the convolution comprises:
    performing convolution calculation on the feature maps output by the convolutional layers to obtain input feature maps of N feature layers corresponding to the convolutional layers;
    performing a convolution calculation on an input feature map of a feature layer representing a lowest resolution to obtain an input feature map of an $N+1^{th}$ feature layer; and
    performing a convolution calculation on the input feature map of the $N+1^{th}$ feature layer to obtain an input feature map of an $N+2^{th}$ feature layer.

4. The method according to claim 1, wherein the method further comprises:
    performing a convolution calculation on the output feature map of each of the feature layers to obtain a final feature of each of the feature layers; and
    transferring the final feature of each of the feature layers to a regional proposal network for target detection.

5. The method according to claim 1, wherein the Backbone network comprises at least one of: ResNet, DenseNet, or EfficientNet.

6. An electronic device, comprising:
    at least one processor; and
    a memory communicatively connected to the at least one processor,
    wherein the memory stores instructions executable by the at least one processor, the instructions, when executed by the at least one processor, cause the at least one processor to perform an operation for fusing features applied to small target detection, comprising:
        acquiring feature maps output by convolutional layers in a Backbone network;
        performing a convolution on the feature maps to obtain input feature maps of feature layers, the feature layers representing resolutions of the input feature maps; and
        fusing, based on densely connection feature pyramid network features, the input feature maps of each feature layer to obtain output feature maps of the feature layer, comprising:
            sampling an input feature map of an $i^{th}$ feature layer and input feature maps of other feature layers having resolutions lower than a resolution corresponding to the $i^{th}$ feature layer, i being a positive integer;
            scaling, after the sampling, the input feature maps of the other feature layers to a same size as the input feature map of the $i^{th}$ feature layer; and
            superimposing the input feature maps of the other feature layers after scaling and the input feature map of the $i^{th}$ feature layer one by one, and using a superimposed final result as an output feature map of the $i^{th}$ feature layer.

7. The device according to claim 6, wherein, the acquiring comprises:
    extracting feature maps of last N convolutional layers from the Backbone network and using the extracted feature maps as feature maps output by the convolutional layers, wherein, N is a positive integer.

8. The device according to claim 7, wherein performing the convolution comprises:
    performing convolution calculation on the feature maps output by the convolutional layers to obtain input feature maps of N feature layers corresponding to the convolutional layers;
    performing a convolution calculation on an input feature map of a feature layer representing a lowest resolution to obtain an input feature map of an $N+1^{th}$ feature layer; and
    performing a convolution calculation on the input feature map of the $N+1^{th}$ feature layer to obtain an input feature map of an $N+2^{th}$ feature layer.

9. The device according to claim 6, wherein the operation further comprises:
    performing a convolution calculation on the output feature map of each of the feature layers to obtain a final feature of each of the feature layers; and transferring the final feature of each of the feature layers to a regional proposal network for target detection.

10. The device according to claim 6, wherein the Backbone network comprises at least one of: ResNet, DenseNet, or EfficientNet.

11. A non-transitory computer readable storage medium, storing computer instructions, the computer instructions, being used to cause a computer to perform an operation for fusing features applied to small target detection, comprising:
   acquiring feature maps output by convolutional layers in a Backbone network;
   performing a convolution on the feature maps to obtain input feature maps of feature layers, the feature layers representing resolutions of the input feature maps; and
   fusing, based on densely connection feature pyramid network features, the input feature maps of each feature layer to obtain output feature maps of the feature layer, comprising:
      sampling an input feature map of an $i^{th}$ feature layer and input feature maps of other feature layers having resolutions lower than a resolution corresponding to the $i^{th}$ feature layer, i being a positive integer;
      scaling, after the sampling, the input feature maps of the other feature layers to a same size as the input feature map of the $i^{th}$ feature layer; and
      superimposing the input feature maps of the other feature layers after scaling and the input feature map of the $i^{th}$ feature layer one by one, and using a superimposed final result as an output feature map of the $i^{th}$ feature layer.

12. The medium according to claim 11, wherein, the acquiring comprises:
   extracting feature maps of last N convolutional layers from the Backbone network and using the extracted feature maps as feature maps output by the convolutional layers, wherein, N is a positive integer.

13. The medium according to claim 12, wherein performing the convolution comprises:
   performing convolution calculation on the feature maps output by the convolutional layers to obtain input feature maps of N feature layers corresponding to the convolutional layers;
   performing a convolution calculation on an input feature map of a feature layer representing a lowest resolution to obtain an input feature map of an $N+1^{th}$ feature layer; and
   performing a convolution calculation on the input feature map of the $N+1^{th}$ feature layer to obtain an input feature map of an $N+2^{th}$ feature layer.

14. The medium according to claim 11, wherein the operation further comprises:
   performing convolution calculation on the output feature map of each of the feature layers to obtain a final feature of each of the feature layers; and
   transferring the final feature of each of the feature layers to a regional proposal network for target detection.

15. The medium according to claim 11, wherein the Backbone network comprises at least one of: ResNet, DenseNet, or EfficientNet.

* * * * *